United States Patent [19]

Hogt et al.

[11] Patent Number: 5,157,087
[45] Date of Patent: * Oct. 20, 1992

[54] ORGANIC PEROXIDES AND THEIR USE IN THE PREPARATION OF EPOXIDE GROUPS-CONTAINING (CO)POLYMERS

[75] Inventors: Andreas H. Hogt, Enschede; John Meijer; Johannes P. J. Verlaan, both of Deventer, all of Netherlands

[73] Assignee: Akzo N.V., Netherlands

[*] Notice: The portion of the term of this patent subsequent to Aug. 6, 2008 has been disclaimed.

[21] Appl. No.: 692,907

[22] Filed: Apr. 29, 1991

Related U.S. Application Data

[63] Continuation of Ser. No. 217,135, Jul. 5, 1988, which is a continuation of Ser. No. 937,973, Dec. 4, 1986, abandoned.

[51] Int. Cl.$^5$ .............................................. C08F 8/08
[52] U.S. Cl. .................................... 525/298; 525/391; 525/392
[58] Field of Search ........................ 525/298, 391, 392

[56] References Cited

U.S. PATENT DOCUMENTS

| | | |
|---|---|---|
| 2,516,649 | 7/1950 | Rust et al. |
| 3,896,176 | 7/1975 | Sacrini et al. |
| 4,119,657 | 10/1978 | Komai et al. |
| 4,384,146 | 5/1983 | Tang |
| 5,037,892 | 8/1991 | Hogt et al. .................. 525/298 |

FOREIGN PATENT DOCUMENTS 8503477 8/1985 PCT Int'l Appl.

OTHER PUBLICATIONS

Tomoi et al., "Synthesis and Crosslinking of Polystyrenes Containing A Pendant Epoxy Group", Makromol. Chem., Rapid Commun. 7, 1986, pp. 143–148.

"Incorporation of Amine Antioxidants Into Natural Rubber Network via Expoxide Groups", Journal of Polymer Science: Polymer Letters Edition, vol. 22, 1984, pp. 327–334.

Chem. Abstracts 109283x, vol. 80, 1974, p. 31.

Burfield et al., "Epoxidation of Natural Rubber Latices: Methods of Preparation and Properties of Modified Rubbers", Journal of Applied Polymer Science, vol. 29, 1984, pp. 1661–1673.

"Challenging Time for Natural Rubber", Rubber Developments, vol. 38, No. 2, 1985, pp. 48–50.

Baker et al., "Epoxidized Natural Rubber-A New Synthetic Polymer?", Rubber World, 191(6), Mar. 1985, pp. 15–20.

"Studies on Grafting Glycidyl Methacrylate on Polyvinyl Chloride Backbones", Journal of Polymer Science, vol. 61, 1962, pp. 185–194.

"Reactive Polymers I.", Die Angewandte Makromolekulare Chemie 48, 1975, pp. 135–143.

"Chemical Reactions of Polymers", Interscience Publishing Co., New York, Chapter II, 1964.

Montaudon et al., "Addition Radicalaire au peroxyde d'allyle et de t-butyle: synthese d'epoxydes fonctionnels", Bull. Soc. Chim. FR, 2, 1985, pp. 198–202.

E. Montaudon et al., "Free-Radical Addition Onto Allyl T-Butyl Peroxide: Synthesis of Functional Epoxides", Bull. Soc. Chim. France, 1985, No. 2, pp. 198–202.

Primary Examiner—Bernard Lipman
Attorney, Agent, or Firm—Oliff & Berridge

[57] ABSTRACT

Novel organic peroxides of the general formula

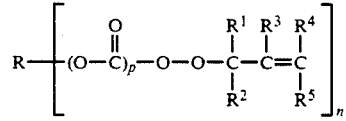

wherein p=0 or 1 and n=1, 2, 3 or 4 are described. These peroxides are excellently suitable for use in the preparation of epoxide groups-containing (co)polymers. Also described are shaped objects obtained by using (co)polymers thus modified.

3 Claims, No Drawings

ORGANIC PEROXIDES AND THEIR USE IN THE PREPARATION OF EPOXIDE GROUPS-CONTAINING (CO)POLYMERS

This is a continuation of application Ser. No. 07/217,135, filed Jul. 5, 1988, which is a continuation of application Ser. No. 06/937,973 filed Dec. 4, 1986 (now abandoned).

The invention relates to novel organic peroxides, to a process of preparing epoxide groups-containing (co)polymers employing these peroxides and to shaped objects.

It is generally known that the introduction of epoxide groups into the appropriate (co)polymers may lead to improved physical and chemical properties of the (co)polymers. According to Rubber World 191(6) pp. 15-20 (1985) and Rubber Developments, Vol. 38 No. 2, pp. 48-50 (1985), for instance, the introduction of epoxide groups into natural rubber leads to advantages such as an increased glass transition temperature, increased oil resistance, reduced gas permeability, improved resilience, increased tensile strength, and improved adhesion to other materials, such as silica fillers, glass fibres and other polymers, more particularly PVC, which is of importance to the preparation of polymeric blends. Further, the polymers thus modified permit carrying out chemical reactions that are typical of epoxy groups. As examples thereof may be mentioned: i) cross-linking the polymer with polyfunctional compounds containing active hydrogen atoms, such as polyamines and dibasic acids, which is described in Chemical Reactions of Polymers, E. M. Fettes (ed.), Interscience Publications, New York (1964), Chapter II, part E, pp. 152 et. seq., ii) covalently bonding to the polymer of antioxidants having amino groups in the molecule, which is described in Journal of Polymer Science, Polymer Letters Edition, Vol. 22, 327-334 (1984) and iii) reacting with fluorine-containing compounds, such as trifluoroacetic acid, resulting in a polymer with improved lubricity and ozon resistance, which is described in WO 85/03477.

Generally, epoxide groups are introduced into (co)polymers by so-called epoxidation reactions, in which an unsaturated (co)polymer in the form of a latex or dissolved in an organic solvent is brought into reaction with a double bond epoxidizing reagent, such as a lower aliphatic peroxy carboxylic acid. To this method, however, there are several disadvantages. First of all, the requirement that the (co)polymer should be unsaturated implies that only a very limited number of (co)polymers can be provided with epoxide groups. For instance, the entire group of saturated (co)polymers is excluded from being functionalized by that route. In the second place, the use of solvents implies that the epoxidation reaction must be followed by a purification step. In addition to the drawbacks to such a step from the point of view of processing technique there are the obvious disadvantages to the use of solvents from the point of view of energy consumption and environmental pollution. In the third place, the epoxidation reaction is always attended with side reactions, such as the formation of hydroxyl groups, acyloxy groups, ether groups, keto groups and aldehyde groups, which detracts from the envisaged object of introducing epoxide groups.

Finally, it should be mentioned that it is well-known to prepare epoxide groups-containing (co)polymers by copolymerizations and graft polymerizations with monomers containing a glycidyl group (Cf. Journal of Polymer Science, Vol. 61, pp. 185-194 (1962), Makromol. Chem., Rapid Commun. 7, pp. 143-148 (1986) and Die Angewandte Makromolekulare Chemie 48, pp. 135-143 (1975)). The inevitable attendant formation, however, of undesirable side products, such as the formation of homopolymers of the glycidyl group-containing monomer, is considered a drawback in actual practice. Moreover, these methods permit preparation of only a limited group of modified (co)polymers.

The invention has for its object to eliminate the above drawbacks to the well-known methods of introducing epoxide groups into (co)polymers and to that end it provides novel organic peroxides. The peroxide according to the invention corresponds to the general formula $$R - \left[ (O-\overset{O}{\underset{\|}{C}})_p - O - O - \overset{R^1}{\underset{R^2}{\overset{|}{C}}} - \overset{R^3}{\underset{|}{C}} = \overset{R^4}{\underset{R^5}{\overset{|}{C}}} \right]_n \quad (I)$$

wherein
p=0 or 1;
n=1, 2, 3 or 4;
$R^1$ and $R^2$ may be the same or different and represent alkyl groups containing 1-4 carbon atoms or together represent a pentamethylene bridge;
$R^3$, $R^4$ and $R^5$ may be the same or different and represent hydrogen atoms or alkyl groups containing 1-4 carbon atoms;
when p=0 and n=1,
R=a t-alkyl group substituted or not with a hydroxyl group and containing 4-18, preferably 4-12 carbon atoms, p-menth-8-yl, a t-alkenyl group containing 5-18, preferably 5-12 carbon atoms, 1-vinylcyclohexyl or a group of the general formula

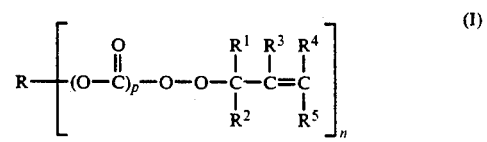

wherein m=0, 1 or 2 and $R^6$ represents an isopropenyl group or a 2-hydroxyisopropyl group;
when p=0 and n=2,
R=an alkylene group with 8-12 carbon atoms which at both ends has a tertiary structure, an alkynylene group with 8-12 carbon atoms which at both ends has a tertiary structure, a group of the general formula

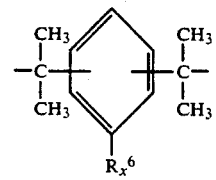

wherein x=0 or 1 and $R^6$ has the above-indicated meaning or
a group of the general formula

wherein $R^7$ and $R^8$ may be the same or different and represent alkyl groups substituted or not with an alkoxy group or an alkoxycarbonyl group and containing 1-10 carbon atoms or together represent an alkylene bridge substituted or not with one or more methyl groups and containing 4-11 carbon atoms;

when p=0 and n=3,
R = 1,2,4-triisopropylbenzene-α,α',α"-triyl or 1,3,5-triisopropylbenzene-α,α',α"-triyl;

when p=0 and n=4,
R = 2,2,5,5-hexanetetrayl;

when p=1 and n=1,
R = an alkyl group substituted or not with a chlorine atom, an alkoxy group, a phenyl group or a phenoxy group and containing 1-18, preferably 3-8 carbon atoms, an alkenyl group containing 3-18, preferably 3-8 carbon atoms, a cyclohexyl group substituted or not with one or more alkyl groups containing 1-4 carbon atoms or cyclododecyl;

when p=1 and n=2,
R = an alkylene group containing 2-12, preferably 2-8 carbon atoms,

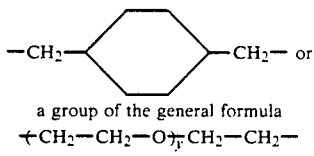

a group of the general formula $+CH_2-CH_2-O+_yCH_2-CH_2-$ wherein y=1-5;

when p=1 and n=3,
R = a group of the general formula $R^9$ C(CH$_2$—)$_3$ wherein $R^9$ represents an alkyl group having 1-5 carbon atoms.

The alkyl groups, alkenyl groups and alkylene groups may be linear or branched, unless otherwise indicated. In view of sterical requirements it should be noted that when there is an aromatic ring in the molecule (see above with p=0/n=1 and p=0/n=2), the ring substituents must in the case of disubstitution not be in a position ortho relative to each other and in the case of trisubstitution not be in three adjacent positions.

It should be added that Bull. Soc. Chim. France No. 2, 198-202 (1985) makes mention of t-butyl allyl peroxide being capable of 2,3-epoxypropanating organic solvents with labile hydrogen atoms. As solvents are mentioned cyclohexane, tetrahydrofuran, propionic acid, propionic anhydride, methyl propionate, acetonitrile and chloroform. The article also mentions the need for the presence of an auxiliary initiator having a decomposition temperature lower than that of the t-butyl allyl peroxide. But this article does not refer to the present invention. Moreover, the peroxide described in it is rather difficult to prepare.

The Peroxides

The peroxides according to the invention correspond to the above-described formula (I) and are selected from the classes of the dialkyl peroxides and diperoxy ketals (p=0) and peroxycarbonates (p=1). They may be prepared in the usual manner. Use is generally made then of a t-alkenyl hydroperoxide of the general formula

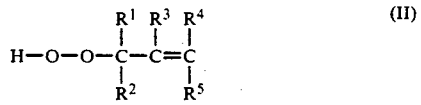

wherein $R^1$–$R^5$ have the above-indicated meaning. The t-alkenyl hydroperoxides in their turn also may be prepared in the usual manner, use being made of a t-alkenyl alcohol and hydrogen peroxide in the presence of a strongly acid catalyst such as sulphuric acid. As examples of suitable t-alkenyl hydroperoxides may be mentioned:

2-methyl-3-buten-2-yl hydroperoxide,
3-methyl-1-penten-3-yl hydroperoxide,
3,4-dimethyl-1-penten-3-yl hydroperoxide,
3-ethyl-1-penten-3-yl hydroperoxide,
3-isopropyl-4-methyl-1-penten-3-yl hydroperoxide,
3-methyl-1-hexen-3-yl hydroperoxide,
3-n-propyl-1-hexen-3-yl hydroperoxide,
1-vinylcyclohexyl hydroperoxide,
2-methyl-3-penten-2-yl hydroperoxide and
2,3,4-trimethyl-3-penten-2-yl hydroperoxide.

As the starting alcohol is readily available, it is preferred that use should be made of 2-methyl-3-buten-2-yl hydroperoxide ($R^1$ and $R^2$ representing methyl groups and $R^3$, $R^4$ and $R^5$ hydrogen atoms).

In the preparation of a number of the present dialkyl peroxides a t-alkenyl hydroperoxide (II) can be reacted in a usual way with an alcohol in an acid medium. As examples of suitable alcohols may be mentioned:
α-hydroxyisopropylbenzene,
1,3-di(α-hydroxyisopropyl)benzene,
1,4-di(α-hydroxyisopropyl)benzene,
1,3,5-tri(α-hydroxyisopropyl)benzene,
1-(α-hydroxyisopropyl)-3-isopropenylbenzene,
1-(α-hydroxyisopropyl)-4-isopropenylbenzene,
1-(α-hydroxyisopropyl)-3,5-diisopropenylbenzene,
1,3-di(α-hydroxyisopropyl)-5-isopropenylbenzene,
2-methyl-3-buten-2-ol,
3-methyl-1-penten-3-ol,
3,4-dimethyl-1-penten-3-ol,
3-ethyl-1-penten-3-ol,
3-isopropyl-4-methyl-1-penten-3-ol,
3-methyl-1-hexen-3-ol,
3-n-propyl-1-hexen-3-ol,
1-vinylcyclohexanol,
2-methyl-3-penten-2-ol,
2,3,4-trimethyl-3-penten-2-ol and
p-menthan-8-ol.

Some dialkyl peroxides according to the invention, however, cannot be properly prepared in this manner. In those cases it is preferred that use should be made of a t-alkenyl alcohol of the general formula

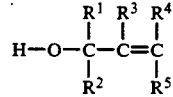

wherein $R^1$–$R^5$ have the above-indicated meaning, which t-alkenyl alcohol is reacted with a hydroperoxide in an acid medium. As examples of suitable hydroperoxides may be mentioned:
t-butyl hydroperoxide, t-amyl hydroperoxide,
2,4,4-trimethylpentyl-2-hydroperoxide,
2,5-dimethyl-2,5-dihydroperoxyhexane and
2,5-dimethyl-2,5-dihydroperoxyhexyne-3.

Typical examples of dialkyl peroxides according to the invention are:
2-(t-amylperoxy)-2-methyl-3-butene,
1-[α-(2-methyl-3-buten-2-ylperoxy)isopropyl]-3-isopropenylbenzene,
1-[α-(2-methyl-3-buten-2-ylperoxy)isopropyl]-4-(α-hydroxyisopropyl)benzene,
1-[α-(2-methyl-3-buten-2-ylperoxy)isopropyl]-3,5-diisopropenylbenzene,
1-[α-(2-methyl-3-buten-2-ylperoxy)isopropyl]-3,5-di(α-hydroxyisopropyl)benzene,
2,5-di(2-methyl-3-buten-2-ylperoxy)-2,5-dimethylhexane,
2,5-di(2-methyl-3-buten-2-ylperoxy)-2,5-dimethylhexyne-3,
1,3-di[α-(2-methyl-3-buten-2-ylperoxy)isopropyl]benzene,
1,4-di[α-(2-methyl-3-buten-2-ylperoxy)isopropyl]benzene,
1,3-di[α-(2-methyl-3-buten-2-ylperoxy)isopropyl]-5-isopropenylbenzene,
1,3-di[α-(2-methyl-3-buten-2-ylperoxy)isopropyl]-5-(α-hydroxyisopropyl)benzene,
1,3,5-tri[α-(2-methyl-3-buten-2-ylperoxy)isopropyl]benzene,
2-(2-methyl-3-buten-2-ylperoxy)-2,4,4-trimethylpentane,
2-(2-methyl-3-buten-2-ylperoxy)-2-methylpentane,
2-(2-methyl-3-buten-2-ylperoxy)-4-hydroxy-2-methylpentane and
8-(2-methyl-3-buten-2-ylperoxy)-p-menthane.

In the preparation of the present diperoxy ketals a t-alkenyl hydroperoxide (II) can be reacted in a usual way with a ketone in an acid medium. As examples of suitable ketones may be mentioned: acetone, methoxyacetone, methyl ethyl ketone, diethyl ketone, methyl isobutyl ketone, n-butyl-4-ketovalerate, 2,5-hexanedione, cyclohexanone, 3,3,5-trimethylcyclohexanone, cyclopentanone and cyclododecanone.

Typical examples of diperoxy ketals according to the invention are:
2,2-di(2-methyl-3-buten-2-ylperoxy)propane,
2,2-di(2-methyl-3-buten-2-ylperoxy)-1-methoxypropane,
2,2-di(2-methyl-3-buten-2-ylperoxy)butane,
1,1-di(2-methyl-3-buten-2-ylperoxy)-3,3,5-trimethylcyclohexane,
1,1-di(2-methyl-3-buten-2-ylperoxy)cyclopentane,
1,1-di(2-methyl-3-buten-2-ylperoxy)cyclododecane,
2,2-di(2-methyl-3-buten-2-ylperoxy)-4-methylpentane,
2,2,5,5-tetra(2-methyl-3-buten-2-ylperoxy)hexane and
4,4-di(2-methyl-3-buten-2-ylperoxy)-n-butylvalerate.

In the preparation of the present peroxycarbonates a t-alkenyl hydroperoxide (II) can be reacted with a chloroformate in the usual way under alkaline conditions. As is known, chloroformates can be prepared from alcohols and phosgene. As examples of suitable alcohols may be mentioned methanol, n-propanol, sec.butanol, isobutanol, n-tetradecanol, n-hexadecanol, 2-chloroethanol, methallylalcohol, 3-methyl-2-buten-1-ol, 3-methyl-3-buten-1-ol, 2-phenylethanol, 2-phenoxyethanol, 3,5,5-trimethylhexanol, ethylene glycol, diethylene glycol, triethylene glycol, tetraethylene glycol, 1,2-propanediol, 1,3-propanediol, 1,4-butanediol, 1,5-pentanediol, 2,5-hexanediol, 1,8-octanediol, 1,10-decanediol, 1,12-dodecanediol, 2,2-dimethyl-1,3-propanediol, 1,4-di(hydroxymethyl)cyclohexane and 1,1,1-trimethylolpropane.

Typical examples of peroxycarbonates according to the invention include:
O-ethyl O,O-(2-methyl-3-buten-2-yl) monoperoxycarbonate,
O-(n-butyl) O,O-(2-methyl-3-buten-2-yl) monoperoxycarbonate,
O-(n-hexyl) O,O-(2-methyl-3-buten-2-yl) monoperoxycarbonate,
O-(n-decyl) O,O-(2-methyl-3-buten-2-yl) monoperoxycarbonate,
O-(n-dodecyl) O,O-(2-methyl-3-buten-2-yl) monoperoxycarbonate,
O-(n-octadecyl) O,O-(2-methyl-3-buten-2-yl) monoperoxycarbonate,
O-(3-methyl-2-buten-1-yl) O,O-(2-methyl-3-buten-2-yl) monoperoxycarbonate,
O-(2-methoxyethyl) O,O-(2-methyl-3-buten-2-yl) monoperoxycarbonate,
O-(3-methoxybutyl) O,O-(2-methyl-3-buten-2-yl) monoperoxycarbonate,
1,2-di[(2-methyl-3-buten-2-yl)peroxycarbonyloxy]ethane,
1,4-di[(2-methyl-3-buten-2-yl)peroxycarbonyloxy]butane,
1,12-di[(2-methyl-3-buten-2-yl)peroxycarbonyloxy]dodecane,
1,8-di[(2-methyl-3-buten-2-yl)peroxycarbonyloxy]-3,6-dioxaoctane and
1,1,1-tri[(2-methyl-3-buten-2-yl)peroxycarbonyloxymethyl)propane.

No particular theory being advanced, it seems plausible that in a rearrangement reaction the peroxides according to the invention are capable of creating epoxide functions:

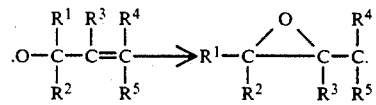

The peroxide according to the invention can be prepared, transported, stored and applied as such or in the form of powders, granules, solutions, aqueous suspensions or emulsions, pastes, etc. Which of these forms is to be preferred partly depends on the case of feeding the peroxide into closed systems. Also considerations of safety (desensitizing) may play a role. As examples of suitable desensitizing agents may be mentioned solid carrier materials, such as silica, chalk and clay, paraffinic hydrocarbons, such as isododecane and white spirit, plasticizers, such as phthalic esters, and water.

Modification of (Co)Polymers

The present peroxides are excellently suitable for use in the preparation of epoxide groups-containing (co)polymers, in which process a "non-modified" (co)polymer is brought into contact with a peroxide according to the invention, upon which the peroxide will entirely or almost entirely be decomposed. The peroxide may be brought into contact with the (co)polymer in various ways, depending on the object of the modification. If, for instance, epoxide groups are to be present on the surface of a (co)polymeric object, the peroxide may be applied to the surface of the material to be modified. It will often be desirable for epoxide groups to be homogeneously distributed in the (co)polymeric matrix. In that case the peroxide may be mixed with the material to be modified, which material may either be in the molten state or, in the case of an elastomer, in the plastic state; to this end use may be made of conventional mixers, such as kneaders, internal mixers and (mixing) extruding equipment. Should the mixing be impeded by a too high melting temperature of the (co)polymer—because of premature peroxide decomposition—it is recommended that first of all the (co)polymer in the solid state should be provided with epoxide groups (see Example 4), after which the modified material is melted and the epoxide groups will be homogeneously distributed in the matrix.

An important practical aspect of the invention is that the moment the peroxide and the (co)polymer are brought into contact with each other and also the moment the peroxide is to be decomposed can be chosen independently of other usual (co)polymer processing steps, such as introducing additives, shaping, etc. First of all, for instance, epoxide groups may be introduced into a (co)polymer employing a peroxide according to the invention and subsequently additives may be introduced, after which the product may be mould processed. However, it is also possible, for instance, for the peroxide according to the invention to be added to the (co)polymer along with other additives and to decompose the peroxide in a following shaping step at elevated temperature, such as extrusion, compression moulding, blow moulding or injection moulding. In the case of (co)polymers that are to be cross-linked, however, care should be taken that the peroxide according to the invention is always present in the (co)polymer prior to cross-linking.

Examples of suitable (co)polymers which can be modified by means of epoxide groups are saturated (co)polymers, such as polyethylene, e.g. LLDPE, MDPE, LDPE and HDPE, polypropylene, both isotactic and atactic, ethylene/vinylacetate copolymer, ethylene/ethylacrylate copolymer, ethylene/methylacrylate copolymer, ethylene/methylmethacrylate copolymer, chlorinated polyethylene, fluorrubber, silicone rubber, polyurethane, polysulphide, polyacrylate rubber, ethylene/propylene copolymer, nylon, polyesters, such as polyethylene terephthalate and polybutylene terephthalate, copolyether esters, poly(butene-1), poly(butene-2), poly(isobutene), poly(methylpentene), polyvinyl chloride, polyvinyl chloride/vinylacetate graft copolymer, polyvinyl chloride/acrylonitrile graft copolymer, and combinations thereof; and unsaturated (co)polymers, such as polybutadiene, polyisoprene, poly(cyclopentadiene), poly(methylcyclopentadiene), partly dehydrochloridated polyvinyl chloride, butadiene/styrene copolymer, acrylonitrile/butadiene/styrene terpolymer, ethylene/propylene/dienemonomer terpolymer, isoprene/styrene copolymer, isoprene/isobutylene copolymer, isoprene/styrene/acrylonitrile terpolymer, polychloroprene, butadiene/acrylonitrile copolymer, natural rubber, and combinations thereof. Also combinations of saturated and unsaturated polymers can be modified according to the invention.

It has been found that due to the invention the favourable effect on the physical and chemical properties as a result of the presence of epoxide groups, which has so far been limited to a relatively small group of (co)polymers (see the introductory part of the description), can now also be obtained with a large group of other (co)polymers.

Particularly suitable (co)polymers to be modified by way of the invention are polyethylene, polypropylene, ethylene/propylene copolymer, ethylene/vinylacetate copolymer, ethylene/propylene/dienemonomer terpolymer and butadiene (co)polymers.

The peroxide according to the invention is generally used in an amount of 0.01 to 15% by weight, preferably 0.1 to 10% by weight, and more particularly 1 to 5% by weight, calculated on the weight of the (co)polymer. Use also may be made of combinations of peroxides according to the invention. Also of advantage may be the presence of an auxiliary peroxide having a decomposition temperature lower than that of the peroxide according to the invention.

The temperature at which the modification is carried out is generally in the range of 50° to 250° C., preferably 100° to 200° C., care being taken then that in order to obtain optimum results the duration of the modification step is at least five half-life periods of the peroxide. As mentioned above, the (co)polymer may in addition to the peroxide contain usual additives. As examples of such additives may be mentioned: stabilizers, such as inhibitors against oxidative, thermal and UV degradation, lubricants, release agents, colorants, reinforcing or non-reinforcing fillers, such as silica, clay, chalk, carbon black and fibrous materials, nucleating agents, plasticizers, cross-linking agents, such as peroxides such as peroxides and sulphur, accelerators and cross-linking coagents, extender oils and pH controlling substances, such as calcium carbonate. These additives may be employed in the usual amounts.

The invention is further described in the following examples.

EXAMPLE 1

Preparation of 2-(t-butylperoxy)-2-methyl-3-butene (peroxide 1)

To a mixture of 9.3 g of t-butyl hydroperoxide and 8.6 g of 2-methyl-3-buten-2-ol stirred at 10° C. were added over a period of 30 minutes 9 g of an aqueous solution of 60% by weight-sulphuric acid. Subsequently, the reaction mixture was stirred for 2 hours at 20° C. Then 25 ml of water were added. The organic phase was separated and washed with aqueous sodium hydroxide and, finally, with water. Obtained were 11.2 g of colourless liquid (yield 71%) having a peroxide 1 content determined with G.L.C. of 89%.

Preparation of
2-(2-methyl-3-buten-2-ylperoxy)-2-methyl-3-butene (peroxide 2)

A mixture of 21.0 g of 2-methyl-3-buten-2-yl hydroperoxide and 17.2 g of 2-methyl-3-buten-2-ol was added, with stirring, to 80 g of a solution of 40% by weight-sulphuric acid in water over a period of 30 minutes and at a temperature of 20° C. Subsequently, the reaction mixture was stirred for 4 hours at 30° C. After the mixture had been cooled 50 ml of water and 50 ml of hexane were added. The organic phase was separated and washed with aqueous sodium hydroxide and, finally, with water. After the hexane had been distilled off under reduced pressure 22.5 g of colourless liquid were obtained. This liquid was then purified by fractional distillation, which resulted in 11.3 g of colourless liquid having a peroxide 2 content determined by G.L.C. of 75%.

Preparation of α-(2-methyl-3-buten-2-ylperoxy)isopropylbenzene (peroxide 3)

To a mixture of 10.2 g of 2-methyl-3-buten-2-yl hydroperoxide and 11.0 g of α-hydroxyisopropylbenzene stirred at 20° C. was added 1.0 ml of an aqueous solution of 5% by weight-perchloric acid. Over a period of 20 minutes there were then added batchwise $MgSO_4.2H_2O$ in an amount of in all 7.0 g, after which the reaction mixture was stirred for 4 hours at 40° C. Subsequently, water was added until all the magnesium sulphate had dissolved. The organic phase was separated and washed with aqueous sodium hydroxide and, finally, with water. Obtained were 18.3 g of colourless liquid (yield 100%) having an active oxygen content of 6.85% (calculated: 7,26%).

Preparation of 1-[α-(2-methyl-3-buten-2-ylperoxy)isopropyl]-4-isopropenylbenzene (peroxide 4)

The procedure was the same as described above for peroxide 3, except that use was made of α-hydroxyisopropyl-4-isopropenylbenzene instead of α-hydroxyisopropylbenzene. Obtained was a yellow liquid in a yield of 92% and an active oxygen content of 5.45% (calculated: 6.15%).

Preparation of 1,1-di(2-methyl-3-buten-2-ylperoxy)cyclohexane (peroxide 5)

To a mixture of 20 g of 2-methyl-3-buten-2-yl hydroperoxide and 8.8 g of cyclohexanone stirred at 10° C. there were added over a period of 60 minutes 12.2 g of an aqueous solution of 45% by weight-sulphuric acid. Subsequently, the reaction mixture was stirred for 3 hours, the temperature being kept at 20° C. by cooling. After addition of 50 ml of water and 50 ml of heptane the organic phase was separated and washed with aqueous sodium hydroxide and, finally, with water. The heptane was removed by distillation under reduced pressure at 10° C. Obtained were 15.2 g of colourless liquid (yield 59%) of which the active oxygen content was 10.0% (calculated: 11.2%).

Of each of the peroxides 1-5 the structure was confirmed by NMR and IR spectroscopic analyses. The temperatures at which the half-life periods of decomposition are 10 hours, 1 hour and 0.1 hour are given in Table 1 for each of the peroxides 1-5; the measurements were carried out in 0.1M solutions in chlorobenzene.

TABLE 1

| Peroxide | Temperature (°C.) for $t_{\frac{1}{2}}$ of | | |
|---|---|---|---|
| | 10 hours | 1 hour | 0, 1 hour |
| 1 | 110 | 133 | 158 |
| 2 | 107 | 129 | 154 |
| 3 | 106 | 128 | 152 |
| 4 | 114 | 141 | 172 |
| 5 | 74 | 94 | 116 |

EXAMPLE 2

Preparation of O-(2-ethylhexyl) O,O-(2-methyl-3-buten-2-yl) monoperoxycarbonate (peroxide 6)

To a stirred mixture of 30 g of water, 0.20 moles of 2-methyl-3-buten-2-yl hydroperoxide and 0.17 moles of 2-ethylhexyl chloroformate was added over a period of 90 minutes and at a temperature of 10° C. 0.20 moles of potassium hydroxide in the form of a 45% by weight-aqueous solution of potassium hydroxide. Stirring was continued for another 5 minutes. The organic phase was separated and subsequently washed with an aqueous 10% by weight-potassium hydroxide solution (5 min., 10° C.), an aqueous sodium bisulphite solution (15 min., 10° C.) and a dilute solution in water of sodium bicarbonate (2×). After the organic phase had been dried with $MgSO_4.2H_2O$, 39.5 g of colourless oil were obtained having a peroxide 6 content of 96.3%, corresponding to a yield of 87%.

Preparation of O-(n-hexadecyl) O,O-(2-methyl-3-buten-2-yl) monoperoxycarbonate (peroxide 7)

To a stirred mixture of 60 ml of pentane, 0.150 moles of 2-methyl-3-buten-2-yl hydroperoxide and 0.120 moles of n-hexadecyl chloroformate were added, over a period of 30 minutes and at a temperature of 8°-11° C., 0.155 moles of potassium hydroxide in the form of an aqueous 45% by weight-potassium hydroxide solution. The reaction mixture was subsequently stirred for 135 minutes at 8°-11° C. The organic phase was separated and successively washed with and aqueous 9% by weight-potassium hydroxide solution (10 min., 10° C.), an aqueous 9% by weight-sodium bisulphite solution (10 min., 10° C.) and an aqueous 0.5% by weight-sodium bicarbonate solution (10 min., 10° C.). After the organic phase had been dried with $MgSO_4.2H_2O$, the pentane was evaporated off under reduced pressure (0.5 mm Hg) and at 10° C. Obtained was a white, solid material containing 94.9% of peroxide 7. The yield was 66%.

The same procedure was used to synthesize the following peroxycarbonates:
O-isopropyl O,O-(2-methyl-3-buten-2-yl) monoperoxycarbonate (peroxide 8)
O-(n-octyl) O,O-(2-methyl-3-buten-2-yl) monoperoxycarbonate (peroxide 9)
O-allyl O,O-(2-methyl-3-buten-2-yl) monoperoxycarbonate (peroxide 10)
O-(4-t-butylcyclohexyl) O,O-(2-methyl-3-buten-2-yl) monoperoxycarbonate (peroxide 11)
1,6-di[(2-methyl-3-buten-2-yl)peroxycarbonyloxy]hexane (peroxide 12)
1,5-di[(2-methyl-3-buten-2-yl)peroxycarbonyloxy]-3-oxapentane (peroxide 13)

The peroxides 8-13 were all obtained in the form of colourless liquids.

Of all the peroxides described in this Example the structure was confirmed by NMR and IR spectroscopic analyses. Table 2 gives for each product the yield, the peroxide content and the temperatures at which the half-life period of decomposition is 10 hours, 1 hour and 0.1 hour (0.1M solution in chlorobenzene).

TABLE 2

| Peroxide | Yield (%) | Content (%) | Temperature (°C.) for $t_{\frac{1}{2}}$ of | | |
|---|---|---|---|---|---|
| | | | 10 hours | 1 hour | 0, 1 hour |
| 6 | 87 | 96.3 | 75 | 96 | 120 |
| 7 | 66 | 94.9 | 64 | 91 | 125 |
| 8 | 90 | 97.9 | 76 | 98 | 123 |
| 9 | 97 | 97.0 | 80 | 100 | 124 |
| 10 | 83 | 97.3 | 67 | 87 | 110 |
| 11 | 88 | 96.3 | 76 | 98 | 123 |
| 12 | 90 | 96.5 | 94 | 113 | 135 |

TABLE 2-continued

| Peroxide | Yield (%) | Content (%) | Temperature (°C.) for t½ of | | |
|---|---|---|---|---|---|
| | | | 10 hours | 1 hour | 0, 1 hour |
| 13 | 78 | 94.5 | 72 | 86 | 102 |

EXAMPLE 3

Modification of various (co)polymers with peroxide 6

In a 50 ml-Brabender blendor 41.6 g of (co)polymer and 4.4 g of peroxide 6 were intermixed at a speed of 30 rotor revolutions per minute and over the periods and at the temperatures given in Table 3 for the various (co)polymers. Of the resulting modified (co)polymers the content of epoxide groups was determined in the following way.

In a 250 ml-round bottomed flask about 1 g of product, which had been weighed out to the nearest 1 mg, was dissolved with refluxing in 100 ml of xylene. After the mixture had been cooled to 30° C., 10,00 ml of a solution in 1,4-dioxane of 4N HCl were added, after which the mixture was kept at 50° C. for 48 hours. Subsequently, 50 ml of acetone, 50 ml of water and 5 ml of 4N nitric acid were added with stirring, after which the mixture was titrated potentiometrically, with stirring, with 0.01N silver nitrate, use being made of a combined Ag,AgCl electrode. As blanks titrations were run on the solvent system used and on solutions of samples of the (co)polymers which had previously been treated in the blendor under the conditions given in Table 3, but in the absence of peroxide 6.

The results are mentioned in Table 3.

TABLE 3

| (Co)polymer | Conditions | | Epoxide content (mmoles/100 g (co)polymer) |
|---|---|---|---|
| | time (hours) | temp. (°C.) | |
| polyethylene (Lupolen ® 1810 H, ex BASF) | 1 | 134–137 | 10.1 |
| ethylene/propylene copolymer (Vistalon ® 404, ex Esso) | 2.5 | 104–124 | 4.4 |
| atactic polypropylene (Stamylan ® A-PP10, ex DSM) | 2.5 | 110–111 | 0.93 |
| ethylene/propylene/diene-monomer terpolymer (Keltan ® 740, ex DSM) | 2.5 | 109–110 | 3.4 |
| styrene/butadiene copolymer (Cariflex ® SBR 1500, ex Shell) | 1 | 106–122 | 3.3 |

To find out whether the epoxide groups were covalently bonded to the (co)polymers the following experiment was carried out with the modified polyethylene described in this Example. An amount of 1.100 g of the material was dissolved with refluxing for 1 hour in 150 ml of xylene. The solution while still warm was added to 750 ml of acetone on which the polymer precipitated as a fine, white flakelike material. After filtration and drying the weight was 0.940 g. Potentiometric analysis showed that the epoxide content of the polymer thus purified was 9.7 mmoles/100 g. It may therefore be concluded that practically all epoxide groups were covalently bonded to the polymer.

EXAMPLE 4

Modification of Polypropylene in the Solid State

In a rotating round bottomed flask 40.5 g of polypropylene powder (Moplen ® FLS 20, ex Montepolimeri) were mixed with 4.5 g of peroxide 3 for 2 hours at 150° C. under a nitrogen atmosphere. The resulting product was washed three times for 5 minutes with 500 ml of acetone, after which it was dried for 24 hours in vacuo. Potentiometric analysis, carried out as described in Example 3, showed that the epoxide content was 4.2 mmoles/100 g of polymer.

EXAMPLE 5

Use being made of ten of the peroxides described in the Examples 1 and 2, ethylene/propylene copolymer (Vistalon ® 404) was modified in a 50-ml Brabender blendor at 30 rotor revolutions per minute. The amount of peroxide in each experiment was 40 mmoles per 100 g of copolymer. For peroxide 6 a reaction time of 2.5 hours was used. For the other peroxides the duration of the treatment was 1 hour. The temperatures used in the blendor for the various peroxides are given in Table 4. Table 4 also mentions the epoxide contents of the resulting copolymers, determined as described in Example 3.

TABLE 4

| Peroxide | Temperature (°C.) | Epoxide content (mmoles/100 g copolymer) |
|---|---|---|
| 1 | 133–164 | 7.0 |
| 2 | 135–155 | 6.7 |
| 3 | 130–149 | 6.9 |
| 5 | 111–119 | 7.7 |
| 6 | 104–124 | 4.4 |
| 7 | 118–139 | 5.8 |
| 8 | 102–136 | 6.1 |
| 10 | 110–117 | 2.7 |
| 11 | 111–139 | 6.3 |
| 13 | 92–98 | 1.1* |

*The mixture obtained was not homogenous.

EXAMPLE 6

Effect of Epoxide Modification on the Mechanical Properties of Silica-Filled, Cross-Linked Ethylene/Propylene Copolymer For the experiments described in this Example use was made of copolymers modified with the peroxides 1 and 6 as described in Example 5.

100 g of modified copolymer were mixed with 20 g of silica filler (Perkasil ® SM500, ex Akzo Chemie), 4.2 g of bis(t-butylperoxyisopropyl)benzene (Perkadox ® 14-40 Bpd, ex Akzo Chemie) and 1.0 g of triallyl cyanurate (Perkalink ® 300, ex Akzo Chemie) on a Swabenthan roll for 5 minutes at 40°-50° C. Subsequently, the resulting product was compressed into a 2 mm thick sheet (15 min., 180° C., 15 tons), after which the following properties were measured: hardness in conformity with ASTM-D2240, tensile strength, the 100%, 200% and 300% moduli and the elongation at rupture in conformity with ISO-standard R37, type 2 and the tear strength in accordance with NEN-standard 5603.

The results are listed in Table 5, which also gives the results of a comparative experiment conducted on unmodified ethylene/propylene copolymer.

TABLE 5

| Mechanical properties | Copolymer | | |
|---|---|---|---|
| | mod. with peroxide | | |
| | 1 | 6 | unmodif. |
| Hardness (Shore A) | 53 | 51 | 49 |
| Tensile strength (MPa) | 7.16 | 7.42 | 6.25 |
| Modulus (MPa) 100% | 1.81 | 1.37 | 1.17 |
| Modulus (MPa) 200% | 4.02 | 3.30 | 1.75 |

TABLE 5-continued

| Mechanical properties | Copolymer mod. with peroxide | | |
| --- | --- | --- | --- |
| | 1 | 6 | unmodif. |
| Modulus (MPa) 300% | 6.72 | 6.20 | 2.63 |
| Elong. at rupture (%) | 315 | 330 | 575 |
| Tear strength (N) | 14.2 | 12.0 | 13.1 |

The results given in Table 5 show that, as compared with the product prepared using unmodified copolymer, the products according to the invention display practically the same hardness, tensile strength and tear strength and at the same time display higher modulus values and lower elongation at rupture. This clearly points to an improvement of the adhesion to the silica filler.

EXAMPLE 7

Manufacture of Laminates of Epoxide Modified Polyethylene and Glass Fibre or Nylon Polyethylene (Lupolen ® 1810 H) was modified with epoxide groups, use being made of peroxide 5 and, in another experiment, of peroxide 8.

The modifications were carried out in a 50 ml-Brabender blendor at 30 rotor revolutions per minute over a period of 1 hour. In both experiments the amount of peroxide was 40 mmoles/100 g of polymer. In the case of peroxide 5 the temperature in the blendor was 120°-142° C. and in the case of peroxide 8 it was 121°-151° C. Of each of the resulting polymers a 1 mm thick sheet was laminated for 30 minutes at 180° C. to either side of a glass fibre fabric provided with 1383 finish (ex Silenka).

Further, of each polymer a 1 mm thick sheet was laminated under the same conditions to a 1 mm thick nylon sheet (Akulon ® M258, ex Akzo Plastics).

The laminates were subsequently cooled in a cold press and kept at room temperature for 18 hours. Then the peel strength was determined in conformity with ISO standard R36 (180°). The results are given in Table 6. It also gives the results of comparative experiments carried out with unmodified polyethylene.

TABLE 6

| Polyethylene | Peel strength (N/cm) | |
| --- | --- | --- |
| | glass fibre | nylon |
| modified with peroxide 5 | 2.76 | 0.10 |
| modified with peroxide 8 | 3.12 | 1.97 |
| unmodified | 1.33 | 0.01 |

The data of Table 6 clearly show that the laminates according to the invention display a considerably better adhesion than the laminates made by using unmodified polyethylene.

Such improved adhesion is of great importance to the preparation of (co)polymeric blends (see also Examples 9 and 10) and glass-fibre filled (co)polymers, because the resulting materials exhibit enhanced impact resistance. The use of the (co)polymers modified according to the invention also results in improved adhesion to other reinforcing materials, such as yarns, cords and fabrics. It should be added that (co)polymers modified according to the invention in combination with nylon may with advantage be applied in the manufacture of co-extruded films.

EXAMPLE 8

Adhesion of a Coating to Epoxide Modified Polyethylene

Polyethylene (Lupolen ® 1810 H) was modified with peroxide 5 and, in another experiment, with peroxide 8 in the way described in the fist part of Example 7. Each resulting polymer was compressed into a sheet 1 mm thick over a period of 15 minutes and at a temperature of 130° C.

Subsequently, of each sheet the adhesion to it of a coating was tested as follows. Each sheet was cut into 2 strips measuring 5 cm×2 cm. On one side each strip was at one end and over a total surface area of 1½×2 cm² covered with a coating of the following composition:

20 g of Epikote ® DX 235 (bisphenol A/F epoxy resin, ex Shell)

12 g of Epilink ® 177 (polyaminoamide, ex Akzo Chemie)

0.3 g of Silane ® A1100 (γ-aminopropyl triethoxy silane, ex Union Carbide).

The coated ends of every two strips were clamped together in a screw clamp and kept at 50° C. for 24 hours. Subsequently, the bonding strength was determined by measuring the force needed to separate the strips by means of a Zwick tensile tester.

The results are given in Table 7, which also mentions the results of a comparative experiment conducted with unmodified polyethylene. The results clearly show that the adhesion obtained with the modified polymers according to the invention is greater than that with the unmodified polyethylene.

TABLE 7

| Polyethylene | Bonding strength (N/cm²) |
| --- | --- |
| modified with peroxide 5 | 18.8 |
| modified with peroxide 8 | 28.6 |
| unmodified | 13.7 |

EXAMPLE 9

Blend of Epoxide Modified Polyethylene and a Co-Reactive Polymer

Polyethylene (Lupolen ® 1810 H) was modified with peroxide 6 via epoxide groups in the way described in Example 3. The resulting material was mixed with acrylic acid-modified polyethylene (Primacor ® 1430, ex Dow Chemical) in a weight ratio of 1:1 in a Brabender blendor for 30 minutes at 120° C. and 30 rotor revolutions per minute. Of the resulting blend the apparent melt viscosity was determined in a Göttfert High Pressure Capillary Rheometer, type 2001, at 190° C. and a shear rate of $14.4s^{-1}$. The result is given in Table 8, which also mentions the apparent melt viscosities, measured under the above conditions, of a 1:1 blend of unmodified polyethylene and Primacor ® 1430, which blend was prepared in the same way as described in this Example for the blend according to the invention, and of the respective starting polymers.

TABLE 8

| Polymer or blend | Apparent melt viscosity (Pa.s) |
| --- | --- |
| modified polyethylene/Primacor ® 1430 | $6.6 \times 10^3$ |
| unmodified polyethylene/Primacor ® 1430 | $1.9 \times 10^3$ |
| modified polyethylene | $8.5 \times 10^3$ |

TABLE 8-continued

| Polymer or blend | Apparent melt viscosity (Pa.s) |
| --- | --- |
| unmodified polyethylene | $2.6 \times 10^3$ |
| Primacor ® 1430 | $1.4 \times 10^3$ |

As appears from the data in Table 8, the apparent melt viscosity of the modified polyethylene/Primacor ® 1430 blend is a factor of 1.33 higher than the average apparent melt viscosity of the modified polyethylene and the Primacor ® 1430. Such an increase is distinctly indicative of the occurrence of strong interaction of the two polymers, which has a favourable effect on the material properties, such as form stability at elevated temperature, resistance to solvents, and impact resistance.

It should be added that both the modified polyethylene and the blend of this material with Primacor ® 1430 can be processed by usual extrusion and injection moulding techniques, despite the increased apparent melt viscosity due to the epoxide modification according to the invention.

Finally, general attention is drawn to the advantages offered by the interaction of epoxide modified (co)-polymers and co-reactive polymers in the manufacture of co-extruded film.

EXAMPLE 10

Blend of Epoxide Modified Ethylene/Propylene Copolymer and Nylon

For the experiment described in this Example use was made of ethylene/propylene copolymer modified with peroxide 5 as described in Example 5. This material was mixed with nylon (Akulon ® M258) in a Brabender blendor over 30 minutes at 30 rotor revolutions per minute and at a temperature of 235° C. The weight ratio between the modified copolymer and nylon was 1:5. Subsequently, the resulting blend was compressed into sheets 2 mm thick at a temperature of 260° C., after which the tensile strength, the rupture strength and the elongation at rupture were determined in conformity with ISO standard R37, type 1. The results are given in Table 9, which also mentions the results of a comparative experiment conducted on unmodified ethylene/-propylene copolymer.

TABLE 9

| Mechanical properties | Blend of nylon with | |
| --- | --- | --- |
| | mod. copolymer | unmod. copolymer |
| Tensile strength (MPa) | 39.3 | 39.2 |
| Rupture strength (MPa) | 42.9 | 35.8 |
| Elong. at rupture (%) | 42 | 16 |

The data in Table 9 clearly show that as compared with the blend prepared using unmodified copolymer the blend according to the invention displays a higher rupture strength and a higher elongation at rupture. So the blend according to the invention has a higher toughness, and consequently a higher impact strength.

We claim:

1. A process for the modification of (co)polymers by the introduction of epoxide groups into said (co)polymers, said process employing an organic peroxide, in which process the peroxide is brought into contact with the (co)polymer and the peroxide is decomposed, characterized in that the peroxide is selected from organic peroxides of the formula:

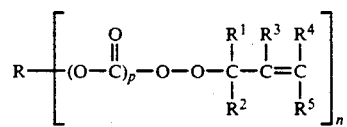

wherein
p=0 or 1
n=1, 2, 3 or 4;
$R^1$ and $R^2$ may be the same or different and represent alkyl groups containing 1-4 carbon atoms or together represent a pentamethylene bridge;
$R^3$, $R_4$ and $R^5$ may be the same or different and represent hydrogen atoms or alkyl groups containing 1-4 carbon atoms;
when p=0 and n=1,
R=a t-alkyl group substituted or not with a hydroxyl group and containing 4-18 carbon atoms,
p-menth-8-yl,
a t-alkenyl group containing 5-18 carbon atoms,
1-vinylcyclohexyl or a group of the formula

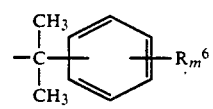

wherein m=0, 1 or 2 and $R^6$ represents an isopropenyl group or a 2-hydroxyisopropyl group;
when p=0 and n=2,
R=an alkylene group with 8-12 carbon atoms which at both ends has a tertiary structure, an alkynylene group with 8-12 carbon atoms which at both ends has a tertiary structure,
a group of the formula

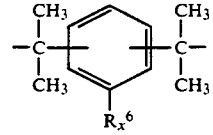

wherein x=0 or 1 and $R^6$ has the above-indicated meaning or
a group of the formula

wherein $R^7$ and $R^8$ may be the same or different and represent alkyl groups substituted or not with an alkoxy group or an alkoxycarbonyl group and containing 1-10 carbon atoms or together represent an alkylene bridge substituted or not with one or more methyl groups and containing 4-11 carbon atoms;
when p=0 and n=3,
R=1,2,4-triisopropylbenzene-α,α',α"-triyl or 1,3,5-triisopropylbenzene-α,α',α"-triyl;

when p=0 and n=4,
R=2,2,5,5-hexanetetrayl;
when p=1 and n=1,
R=an alkyl group substituted or not with a chlorine atom,
an alkoxy group, a phenyl group or a phenoxy group and containing 1-18 carbon atoms,
an aklenyl group containing 3-18 carbon atoms,
a cyclohexyl group substituted or not with one or more alkyl groups containing 1-4 carbon atoms or cyclododecyl;
when p=1 and n=2,
R=an alkylene group containing 2-12 carbon atoms,

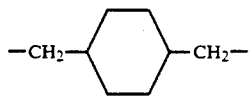

or a group of the formula

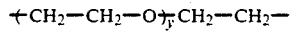

wherein y=1-5;
when p=1 and n=3,
R=a group of the formula $R^9C(CH_2-)_3$ wherein $R^9$ represents an alkyl group having 1-5 carbon atoms.

2. A process according to claim 1, characterized in that $R^1$ and $R^2$ represent methyl groups and $R^3$, $R^4$ and $R^5$ represent hydrogen atoms.

3. A process according to claim 1, characterized in that the peroxide is selected from the group consisting of:
2-(t-butylperoxy)-2-methyl-3-butene,
8-(2-methyl-3-buten-2-ylperoxy)-p-menthane,
2-(2-methyl-3-buten-2-ylperoxy)-2-methyl-3-butene,
α-(2-methyl-3-buten-2-ylperoxy)isopropylbenzene,
1-[α-(2-methyl-3-buten-2-ylperoxy)isopropyl]-4-isopropenyl-benzene,
2,5-di(2-methyl-3-buten-2-ylperoxy)-2,5-dimethylhexane,
1,3-di[α-(2-methyl-3-buten-2-ylperoxy)isopropyl]-benzene,
2,2-di(2-methyl-3-buten-2-ylperoxy)butane,
1,1-di(2-methyl-3-buten-2-ylperoxy)cyclohexane,
1,1-di(2-methyl-3-buten-2-ylperoxy)-3,3,5-trimethylcyclohexane,
O-isopropyl O,O-(2-methyl-3-buten-2-yl) monoperoxycarbonate,
O-(2-ethylhexyl) O,O-(2-methyl-3-buten-2-yl) monoperoxycarbonate,
O-(n-octyl) O,O-(2-methyl-3-buten-2-yl) monoperoxycarbonate,
O-(n-hexadecyl) O,O-(2-methyl-3-buten-2-yl) monoperoxycarbonate,
O-allyl O,O-(2-methyl-3-buten-2-yl) monoperoxycarbonate,
O-(4-t-butylcyclohexyl) O,O-(2-methyl-3-buten-2-yl) monoperoxycarbonate,
1,6-di[(2-methyl-3-buten-2-yl)peroxycarbonyloxy]-hexane and
1,5-di[(2-methyl-3-buten-2-yl)peroxycarbonyloxy]-3-oxapentane.

* * * * *

UNITED STATES PATENT AND TRADEMARK OFFICE
CERTIFICATE OF CORRECTION

PATENT NO. : 5,157,087
DATED : October 20, 1992
INVENTOR(S) : Andreas H. HOGT et al It is certified that error appears in the above-identified patent and that said Letters Patent is hereby corrected as shown below:

Col. 11, line 20, change "10,00" to --10.00--.

Signed and Sealed this

Fifth Day of October, 1993

Attest:

BRUCE LEHMAN

Attesting Officer

Commissioner of Patents and Trademarks